(12) United States Patent
Tornwall et al.

(10) Patent No.: US 9,301,626 B2
(45) Date of Patent: Apr. 5, 2016

(54) CHECKOUT COUNTER

(75) Inventors: Magnus Tornwall, Jonkoping (SE); Carl Von Sydow, Jonkoping (SE); Johan Moller, Huskvarna (SE); Erik Kooi, Amersfoort (NL); Hugo Boiten, Amersfoort (NL)

(73) Assignee: ITAB Scanflow AB, Jonkoping (SE)

( * ) Notice: Subject to any disclaimer, the term of this patent is extended or adjusted under 35 U.S.C. 154(b) by 339 days.

(21) Appl. No.: 13/808,833

(22) PCT Filed: Jun. 23, 2011

(86) PCT No.: PCT/SE2011/050839
§ 371 (c)(1),
(2), (4) Date: Jun. 14, 2013

(87) PCT Pub. No.: WO2012/005660
PCT Pub. Date: Jan. 12, 2012

(65) Prior Publication Data
US 2015/0062560 A1 Mar. 5, 2015

(30) Foreign Application Priority Data

Jul. 8, 2010 (SE) ........................ 1050766
Oct. 19, 2010 (SE) ........................ 1051090

(51) Int. Cl.
*G01J 3/00* (2006.01)
*A47F 9/04* (2006.01)
(Continued)

(52) U.S. Cl.
CPC . *A47F 9/047* (2013.01); *G01J 3/28* (2013.01); *G01N 21/255* (2013.01); *G01N 21/84* (2013.01); *G06Q 20/208* (2013.01); *G07G 1/0054* (2013.01)

(58) Field of Classification Search
CPC ............ G01J 3/00; G01J 3/28; G01N 21/255; G01N 21/84
USPC ............................................................ 356/51
See application file for complete search history.

(56) References Cited

U.S. PATENT DOCUMENTS 3,867,041 A * 2/1975 Brown et al. ................. 356/448
4,676,343 A * 6/1987 Humble et al. ................. 186/61
(Continued)

FOREIGN PATENT DOCUMENTS

CA 2054851 A1 5/1993
CA 2110733 A1 6/1994
(Continued)

OTHER PUBLICATIONS

Translation of the First Office Action for CN Application 201180033877.5.
(Continued)

*Primary Examiner* — Roy M Punnoose
(74) *Attorney, Agent, or Firm* — Thompson Coburn LLP

(57) ABSTRACT

A classification device (2) for identification of articles (3) in an automated checkout counter is presented. The device comprises a memory unit (5) capable of storing digital reference signatures, each of which digital reference signatures corresponds to an article identity, a processor (6) connected to the memory unit (5), and at least one sensor (4, 7, 14, 15, 16, 17, 18, 24) configured to determine a measured signature of an article (3) wherein said processor (6) is configured to compare said measured signature with the digital reference signatures, and to calculate a matching probability of a predetermined number of article identities.

11 Claims, 5 Drawing Sheets

Fig. 2

(51) Int. Cl.
 *G07G 1/00* (2006.01)
 *G06Q 20/20* (2012.01)
 *G01N 21/25* (2006.01)
 *G01J 3/28* (2006.01)
 *G01N 21/84* (2006.01)

(56) References Cited

U.S. PATENT DOCUMENTS

| | | | |
|---|---|---|---|
| 4,964,053 A | 10/1990 | Humble | |
| 5,497,314 A * | 3/1996 | Novak | 705/17 |
| 5,662,190 A * | 9/1997 | Abe | 186/61 |
| 5,867,265 A * | 2/1999 | Thomas | 356/328 |
| 6,069,696 A | 5/2000 | McQueen et al. | |
| 6,075,594 A * | 6/2000 | Thomas | G07G 1/0054 356/328 |
| 6,155,489 A | 12/2000 | Collins, Jr. et al. | |
| 6,260,023 B1 * | 7/2001 | Seevers et al. | 705/20 |
| 6,363,366 B1 * | 3/2002 | Henty | 705/400 |
| 6,408,279 B1 | 6/2002 | Mason | |
| 6,412,694 B1 | 7/2002 | Kumar | |
| 6,431,446 B1 | 8/2002 | Gu et al. | |
| 6,457,644 B1 | 10/2002 | Collins, Jr. et al. | |
| 6,497,362 B2 | 12/2002 | Persky et al. | |
| 6,510,994 B1 | 1/2003 | Zhu et al. | |
| 6,529,855 B1 | 3/2003 | Gu | |
| 6,577,983 B1 | 6/2003 | Zhu | |
| 6,601,767 B1 | 8/2003 | Gu et al. | |
| 6,606,579 B1 | 8/2003 | Gu | |
| 6,668,078 B1 | 12/2003 | Bolle et al. | |
| 6,837,428 B2 | 1/2005 | Lee et al. | |
| 6,845,910 B2 | 1/2005 | Gu et al. | |
| 7,044,370 B2 | 5/2006 | Bellis, Jr. et al. | |
| 7,103,207 B2 | 9/2006 | Brown et al. | |
| 7,118,026 B2 * | 10/2006 | Harris et al. | 235/375 |
| 7,218,395 B2 | 5/2007 | Kaye et al. | |
| 7,248,754 B2 | 7/2007 | Cato | |
| 7,319,990 B1 * | 1/2008 | Henty | 705/400 |
| 7,337,960 B2 | 3/2008 | Ostrowski et al. | |
| 7,434,663 B1 | 10/2008 | Brosnan et al. | |
| 7,492,973 B2 | 2/2009 | Cato | |
| 7,527,207 B2 * | 5/2009 | Acosta et al. | 235/462.31 |
| 7,546,250 B1 | 6/2009 | Brosnan et al. | |
| 7,909,248 B1 | 3/2011 | Goncalves | |
| 8,113,427 B2 | 2/2012 | Ross et al. | |
| 8,118,226 B2 | 2/2012 | Olmstead et al. | |
| 8,196,822 B2 | 6/2012 | Goncalves | |
| 8,430,311 B2 | 4/2013 | Ostrowski et al. | |
| 8,462,212 B1 * | 6/2013 | Kundu et al. | 348/150 |
| 8,474,715 B2 | 7/2013 | Goncalves | |
| 8,498,903 B2 | 7/2013 | Edwards | |
| 8,608,077 B2 | 12/2013 | Olmstead | |
| 8,927,882 B2 * | 1/2015 | Teraoka | 177/25.13 |
| 2003/0058441 A1 * | 3/2003 | Shakespeare et al. | 356/319 |
| 2003/0158796 A1 * | 8/2003 | Balent | 705/28 |
| 2004/0262391 A1 * | 12/2004 | Harris et al. | 235/454 |
| 2006/0138220 A1 | 6/2006 | Persky | 235/383 |
| 2006/0180670 A1 * | 8/2006 | Acosta et al. | 235/462.31 |
| 2009/0152348 A1 | 6/2009 | Ostrowski et al. | |
| 2011/0078033 A1 | 3/2011 | Bravo | |
| 2012/0087547 A1 | 4/2012 | He et al. | |

FOREIGN PATENT DOCUMENTS

| | | | |
|---|---|---|---|
| EP | 1154262 A1 * | 11/2001 | G01N 21/89 |
| GB | 1334758 A | 10/1973 | |
| JP | H5-231914 | 9/1993 | |
| JP | 06-64645 | 6/1994 | |
| JP | H06180785 A | 6/1994 | |
| JP | H6-333065 | 12/1994 | |
| JP | H9-166490 | 6/1997 | |
| JP | 2000-155767 A | 6/2000 | |
| JP | 2004-535030 A | 11/2004 | |
| JP | 2010-123142 A | 6/2010 | |
| WO | 2012/005659 A1 | 1/2012 | |
| WO | 2012/005660 A1 | 1/2012 | |

OTHER PUBLICATIONS

Translation of the First Office Action for CN Application 201180033868.6.
International Preliminary Report on Patentability (Chapter I) for PCT/SE2011/050838 dated Jan. 8, 2013.
International Preliminary Report on Patentability (Chapter I) for PCT/SE2011/050839 dated Jan. 8, 2013.

* cited by examiner

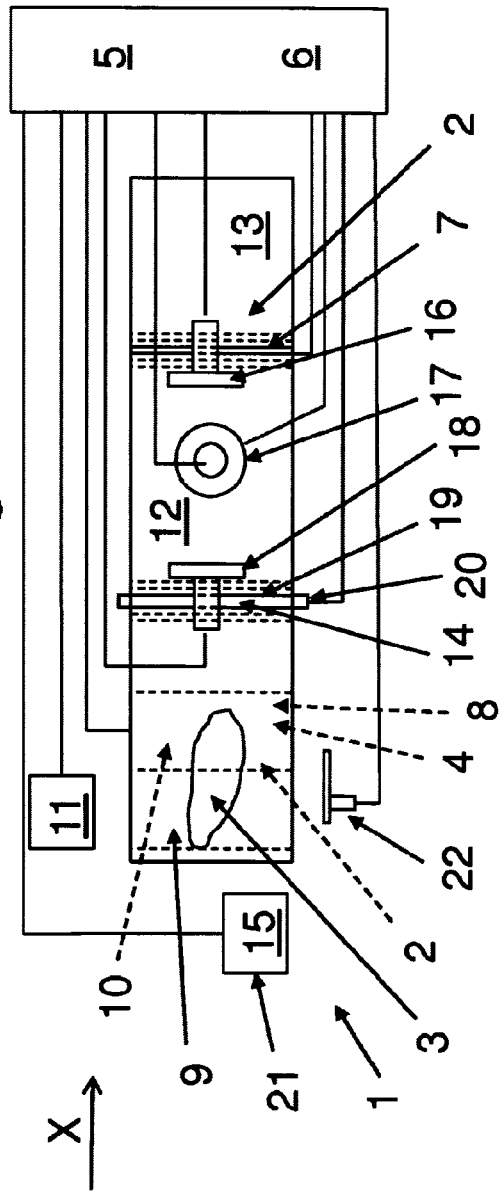
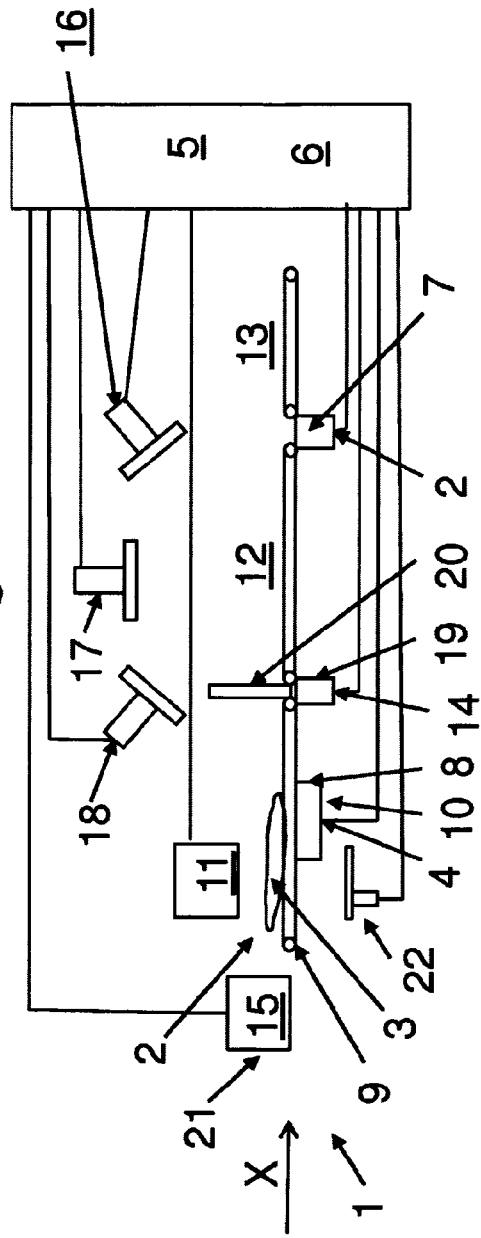

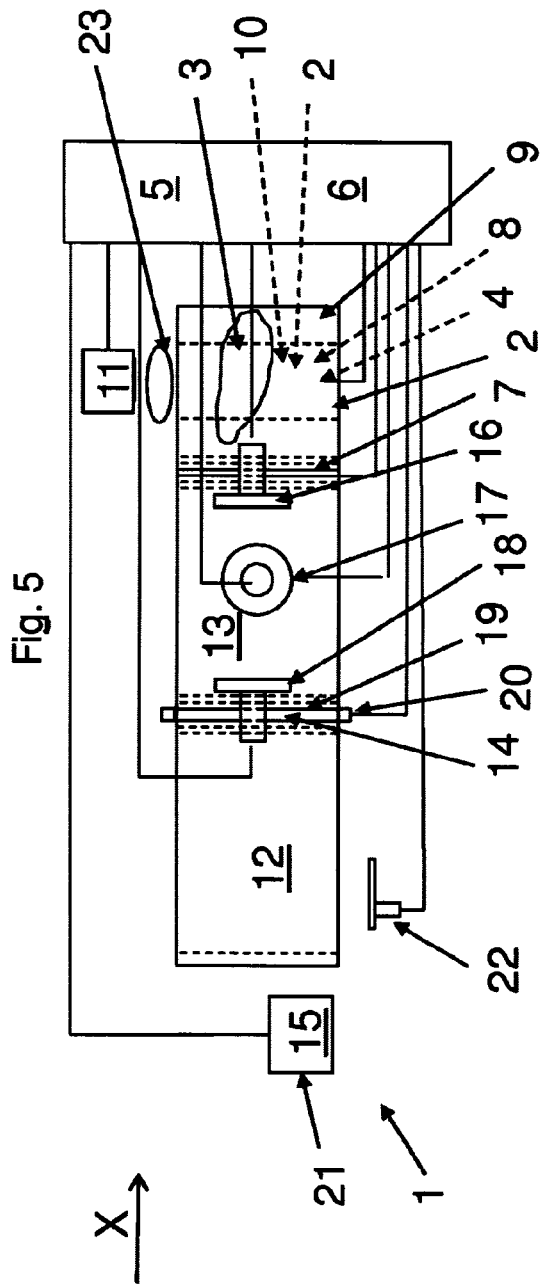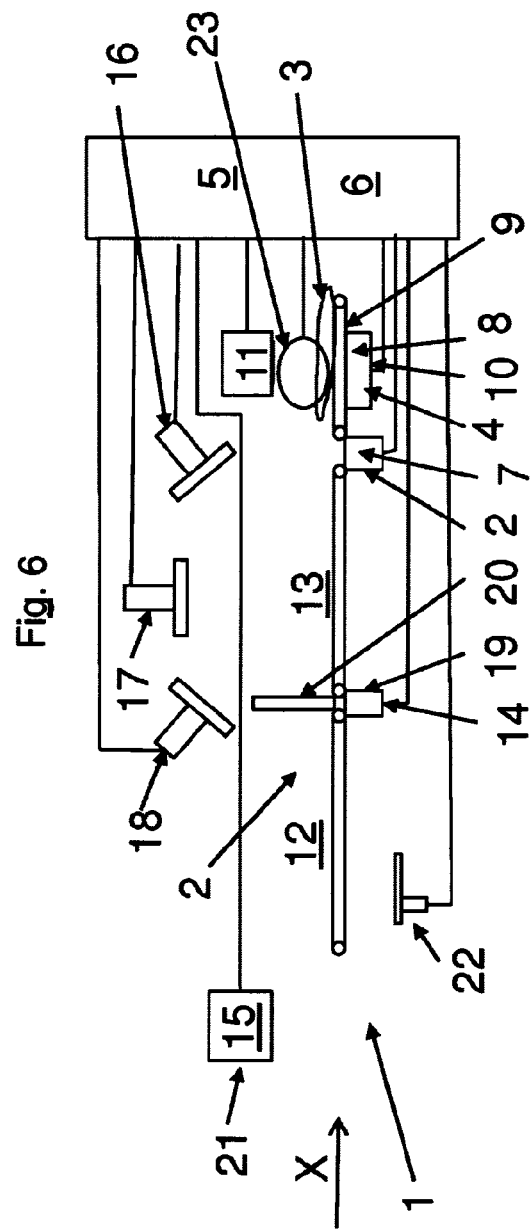

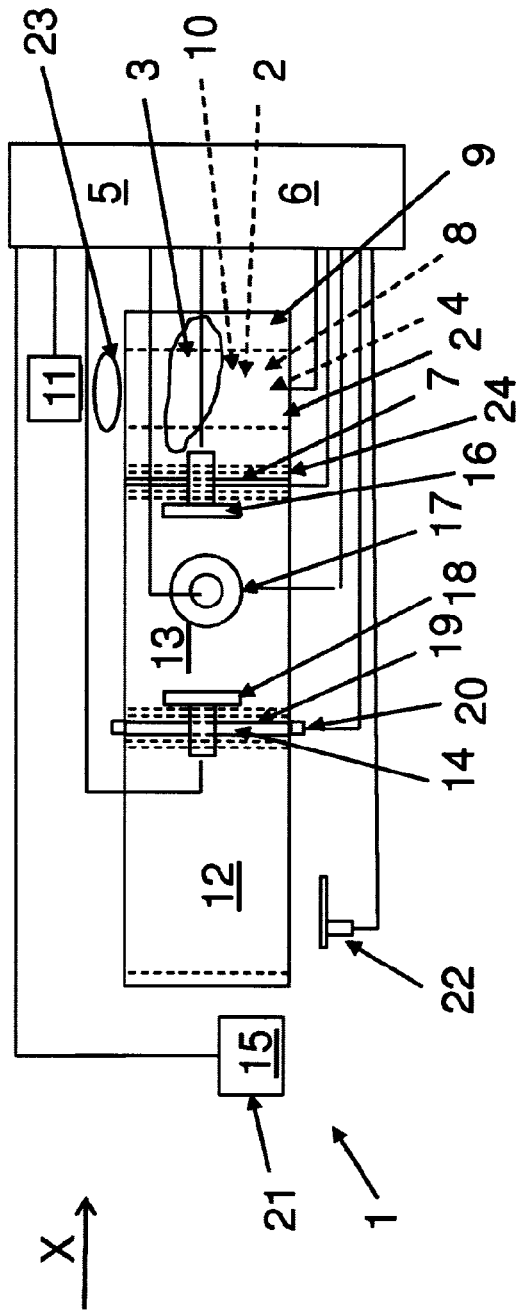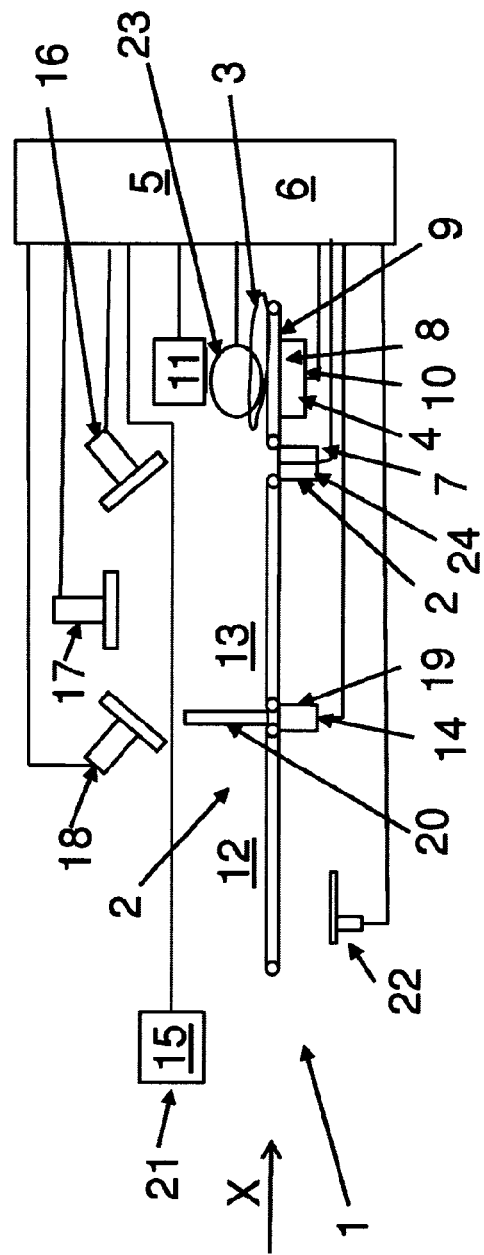

CHECKOUT COUNTER

CROSS-REFERENCE TO RELATED APPLICATIONS

This application is a national stage application of International Patent Application No. PCT/SE2011/050839, published as WO2012/005660, which was filed on Jun. 23, 2011, which claims priority to Swedish Patent Application Nos. 1050766-3 filed Jul. 8, 2010 and 1051090-7 filed Oct. 19, 2010, the disclosures of which are incorporated by reference herein.

TECHNICAL FIELD

The present invention relates to a classification device for identifying articles in an automated checkout counter as well as to an automated checkout counter comprising such classification device. The invention further relates to a method for an automated checkout counter.

BACKGROUND

In today's stores many different types of articles, e.g. vegetables, fruit, and different packages may be purchased. Some stores uses a classification device of an automated checkout counter for identifying the articles. For example, U.S. Pat. No. 4,676,343A describes how to use a conveyor scales together with a laser scanner for reading labels at a checkout counter. The labels are particularly arranged to be read by the laser scanner and comprises information about the weight of the article which should be matched with the actual weight of the article as read by the scales. A problem with the device according to U.S. Pat. No. 4,676,343 is that the laser scanner and the scales must be used for identifying the article, which is resource consuming and creates several interruptions in the process if one of the laser scanner or scales should fail. Another problem is that the particular label must be present on the article, which requires that the customer must attach a label on the article if there is no label. Problems may therefore arise due to wrong handling by the customer. The need of a label further provides a drawback in that the customer may not easily purchase bulk articles but will be required to weigh and identify the articles in order to assure the correctness of the required label.

Other known devices are described in CA2054851, U.S. Pat. No. 5,662,190, US20060138220, and US20040262391.

Classification devices of checkout counters are thus well known, but none of the previously known devices are automated for handling different types of articles such as fruit and packages and at the same time being arranged to provide an optimum degree of security with respect to identification, however still requiring a minimal use of sensor resources.

SUMMARY

With respect to the prior art there is a need for an improved classification device of a checkout counter for automatic identification of articles where the number of incorrect identifications is approaching zero, but where the sensor resources are used optimally for reducing the processor power such that a high processor speed is retained.

The present invention seeks to solve the above mentioned problems by means of a classification device for identification of articles.

According to a first aspect of the invention, a classification device for identification of articles in an automated checkout counter is provided. The classification device comprises a memory unit capable of storing digital reference signatures, each of which digital reference signatures corresponds to an article identity, a processor connected to the memory unit, and at least one sensor configured to determine a measured signature of an article wherein said processor is configured to compare said measured signature with the digital reference signatures, and to calculate a matching probability of a predetermined number of article identities.

According to a second aspect, an automated checkout counter is provided comprising a classification device according to the first aspect.

According to a third aspect of the invention, a method for classifying articles in an automated checkout counter is provided. The method comprises the steps of providing a classification device comprising a memory unit capable of storing digital reference signatures, each of which digital reference signatures corresponds to an article identity, a processor connected to the memory unit, and at least one sensor configured to determine a measured signature of an article, wherein the method comprises the steps of comparing said measured signature with the digital reference signatures, and calculating a matching probability of a predetermined number of article identities.

According to a yet further aspect of the invention, an automated checkout counter comprising a classification device for identification of articles is provided. The classification device comprises a weight sensor for weighing the article, a memory unit comprising information of one or several articles, a processor connected to the memory unit and to the weight sensor, as well as an infrared spectroscopy sensor, from hereon denoted as a NIR sensor and detecting wavelengths from approximately 780 nm to 2500 nm, connected to the processor. The memory unit comprises one or several first signatures created by the first NIR sensor or another NIR sensor, each of which first signatures is connected to a corresponding article identity. The first signatures may be created directly at the checkout counter by using the first NIR sensor, a second NIR sensor, or by storing signatures created by a NIR sensor not connected to the checkout counter in said memory.

When a NIR sensor is used on a certain kind of articles, e.g. a specific type of apple, a first signature will be received which may be coupled to the article and which may be denoted as a specific article identity in the memory unit, like e.g. the name of the article. Each type of article creates a unique first signature which may be coupled to the identity of the article. The first NIR sensor is arranged to create a second signature connected to the article when an article is placed before, on or after the weight sensor. The processor is subsequently arranged to compare the second signature to the first signature in order to identify the article as an existing article identity in the memory unit. The checkout counter is arranged to weigh the article by means of the weight sensor before, during or after the creation of the second signature. The weight of the article is subsequently used by the processor together with the article identity for determining the price of the article.

An advantage of the present invention is that the checkout counter may automatically identify all kinds of articles without the need for a customer to identify the article prior to the checkout counter, e.g. by attaching a bar code. The NIR sensor is particularly valuable for identification of fruit and vegetables, as well as certain types of bulk articles, since such articles have previously required that the customer has identified the article and subsequently labeled it due to the fact that sensors using cameras and image processing have not been capable of determining the identity of the article.

The weight sensor preferably comprises a conveyor scale which automatically conveys and measures the article. The customer will here position the article on the conveyor belt which either weights and subsequently conveys, or conveys, holds, and weights, for later conveying of the article. As previously been mentioned the first NIR sensor may be arranged at the checkout counter before, during, or after weighing. The fastest way is however to allow the first NIR sensor to identify the article when the conveyor belt holds for measuring the article.

According to one embodiment of the invention, as a complement to the NIR sensor and the weight unit, the checkout counter may be equipped with one or several sensors which, if they are used according to the invention, provides the advantage of increased security when identifying the article but with a minimal use of resource and consequently time and energy. It should be mentioned that an article should be identified in less than one second for considering an automated checkout counter to be user friendly by the customers.

The present invention seeks to solve the problem of optimal use of resources with several sensors by using the sensors according to certain predetermined combinations which provides high security in identifying the article as well as high process speed. The combinations also provide the advantage that when a given combination is fulfilled, i.e. the sensor or sensors in combination provides a positive result of identification, the other sensors may be disconnected or directed towards identification of another article, which provides an optimization of the process resources.

The embodiment with several sensors is thus designed on a number of predetermined combinations comprising partial set of existing sensors, where it will be sufficient that one of the predetermined combinations provides a positive result. The sensors may be switch on, i.e. be activated, in sequences in order to find beneficial combinations or partial set of sensors or all sensors may be active until one of the combinations provide a positive result. A positive result should in this context be interpreted as if all sensors of the combination have detected and identified a predetermined property of an article, which properties in combination provide an articles identity. The identity may be determined by means of checking a database comprising properties of a number of articles. Example of properties may include weight, size, color, shape, contour, marking by a barcode and/or text and/or figure and/or pattern.

According to the embodiment the classification device always comprises a weight sensor and a NIR sensor according to above, as well as one or several of: a contour sensor and/or a barcode sensor and/or a symbol reading sensor which uses optical character recognition and (machine) text interpretation and/or a color texture sensor and/or a color histogram sensor and/or a VIS sensor. The symbol reading sensor is from hereon called OCR which is a general known abbreviation of the English term "Optical Character Recognition". The VIS sensor is a spectrometer comprising a light source and a VIS camera, from hereon called a VIS sensor, the VIS sensor is detecting wavelengths from approximately 200 nm to 1100 nm. The spectrum thus overlaps the wavelengths of visual light which extends from 400 nm to 660 nm. Experiments have shown that, at the device according to the invention, the classification device comprising a color texture sensor and/or a color histogram sensor and/or a VIS sensor does not operate satisfactory when the VIS sensor is operating in the complete frequency interval 200 nm-1100 nm since there is a conflict between the color sensors and the VIS sensor in the interval of visual light, i.e. between 400 nm and 660 nm.

The VIS sensor according to the invention is therefore active in the intervals between 200 nm and 400 nm and between 660 nm and 1100 nm when it is combined with the color texture sensor and/or the color histogram sensor. If the color texture sensor and the color histogram sensor are disconnected the VIS sensor may however operate in the complete frequency interval between 200 nm and 1100 nm since there is no conflict. The processor is programmed to control the sensors to achieve optimal efficiency of the classification device.

The sensors cooperate in a way that if the sensors are activated in the following combinations the remaining sensors, except the weight sensor and the NIR sensor, are allowed to be deactivated or not be activated at all, depending on the article being identified:

weight sensor and contour sensor and OCR, or
contour sensor and OCR, or
weight sensor and OCR, or
weight sensor and color histogram sensor and contour sensor, or
weight sensor and contour sensor and OCR, or
weight sensor and color histogram sensor and contour sensor and color texture sensor and OCR and barcode sensor, or
weight sensor and contour sensor and color texture sensor and OCR or
weight sensor and barcode sensor, or
only OCR, or
VIS sensor in combination with any of the above combinations, or
only VIS sensor.

One advantage of the invention is that the combinations provide an optimal high security with a minimal use of resources, which will be explained below.

The symbol reading sensor is connected to a computer/image processing unit which uses an algorithm using information from images from the existing camera or cameras of the device. For articles, which substantially can be unambiguously identified by means of symbol reading, it will be sufficient if the symbol reading sensor, OCR, identifies a symbol and/or a text which then unambiguously identifies the article. Examples of articles which may be identified by only using a symbol reading sensor, OCR, are pre-packaged packages where the customer is not required to perform any procedure, such as refilling or any other procedure. Example of articles where it is not enough with the symbol reading sensor, are some bulk articles where the quantity of the article, i.e. weight, is not known. Further properties of the article may be necessary and may require symbol reading and/or weight and/or color histogram and/or color texture and/or contour. It shall be mentioned that "contour" is defined as a two dimensional projection of a three dimensional object.

Certain articles are thus more difficult to identify than others and depending on the article one or several of the included sensors of the classification device are required.

Preferably, the weight sensor comprises one conveyor scale comprising one conveyor part and one weight unit connected thereto which automatically conveys the article, weighs it and transmit the information of the weight to the database. In this way contributions from workers and customers will be eliminated which removes the need of manual transport of the article over the weight unit. One or several sensors may be connected to the checkout counter for controlling the conveyor scale.

The contour sensor comprises a camera for providing still or moving images and may preferably be a linear camera which reads a horizontally projected surface or a linear camera in combination with an object sensor which consists of a vertical light curtain for reading the vertical projection. The contour sensor is connected to an image processing unit where the contour, i.e. a two dimensional projection of a three dimensional object, is checked against the properties in the database.

The barcode sensor comprises a camera for providing still or moving images. The barcode sensor is connected to an image processing unit where the barcode is checked against the properties in the database.

The symbol reading sensor comprises a camera for providing still or moving images. The symbol reading sensor is connected to an image processing unit where the symbol is checked against the properties in the database.

The color texture sensor comprises a camera for providing still and moving image. The color texture sensor is connected to an image processing unit where the color texture is checked against the properties in the database. The image processing unit comprises an algorithm which calculates where a certain color is present in the image. One common algorithm is "Weibull color texture algorithm", but other algorithms may also be considered.

The color histogram sensor comprises a camera for providing still and moving pictures. The color ratio in the image is usually illustrated by means of a representation, a so-called histogram. A histogram is generated by examination of all pixels of the image, and the number of pixels having a specific color value are summarized.

The above mentioned image processing units may consist of one or several units and may comprise one or several computers with software capable of performing the above mentioned analyzes. The classification device may comprise one or several cameras which are included in the above mentioned sensors. One example of a preferred embodiment is that the contour sensor comprises a first camera positioned in a way that the contour is read when the article passes the camera. According to the invention a linear camera is suitable since the reading then occurs during the conveying of the article between two conveyor belts or over a translucent surface. It is also suitable that the classification device comprises a second camera and possibly several cameras to be able to see the article from different angles for achieving the highest possible reliability when detecting barcode, text and images. The other camera, and if applicable a further camera/cameras, is arranged to record an image or images which will be used by the image processing unit for analyzes of color histogram, color texture, OCR and barcode reading. One further alternative is that the classification device comprises only the first camera and the second camera where the second camera is optically connected to one or several lenses which observe the article from different angles and where the image processing unit analyses the images from corresponding angles. The previously mentioned linear camera, being positioned between the conveyor belts, is however the only camera which may capture if the barcode is positioned downwards on the article.

The NIR sensor operates in such way that infrared light illuminates the article and the reflecting infrared light from the article is being analyzed with reference to phase displacement caused by surface ratio/surface properties and chemical bonds at the article which creates a reflection spectrum. NIR sensors are known per se by prior art.

As mentioned above NIR is a shortening of the English term "Near InfraRed Spectroscopy" and comprises a light source for near infrared light and a NIR camera which may register near infrared light. Near infrared light typically has a wavelength of 580-2500 nm, or preferably 780-1750 nm. The wavelength has shown to be suitable for analyzing bulk material, fruit and vegetables. In this context "NIR" may include the light source and the NIR camera, i.e. the complete NIR arrangement for analyzes. However, "NIR sensor" may only include the sensing equipment, e.g. the light guiding probe and the spectrometer.

By analyzing a known article with a NIR sensor a unique reflection spectrum is received which may be connected to the article. The reflection spectrum may either be used directly as a signature connected to the article or the reflection spectrum is processed to create the signature. An article in a store may look different at different occasions, e.g. an article grow old (eventually fruit will rotten) and the article may be packed in one or several plastic bags or the article may be solitary or in a group, or being arranged in different orientations; natural variations of the article occurs also, etc. The environment for a checkout counter may also be different in different stores, e.g. different amount of light, color, etc. All these parameters provide that a NIR spectrum of a certain article in a certain environment at a certain occasion does not necessarily match with another NIR spectrum of the article in another environment at another occasion. To be able to use a NIR sensor at a checkout counter according to the invention the first signature has to match the second signature at a certain degree such that the processor is able to identify the article by a comparison. It is thus an advantage if the first signature is created in the same environment as the second signature. Since the second signature is created at the checkout counter during use, it is an advantage if the first signature is created during the same conditions. According to the invention, the classification system has thus a self-learning functionality in which the first signature is created by programming the memory unit with an article identity whereafter the article is transported trough the checkout counter during circumstances similar to use, i.e. circumstances for the checkout counter which refers to customer use. To consider the mentioned variations the article is transported several times through the checkout counter and in different variations, e.g. with one or several bags and/or solitary or in a group, etc. Each time the article is transported through the checkout counter and a NIR sensor is analyzing the article a first signature is created, which means that each article identity may be connected to a large amount of first signatures such that the processor will be able to identify the article when comparing it to the second signature and one or more of the first signatures. During learning the first NIR sensor may be arranged to perform the analyses, or a second NIR sensor will be connected. The learning does not need to be performed at the exact location where the checkout counter will be used but may rather be performed at another location.

At the creation of the first and second signature the surroundings will be considered by means of a background spectrum, i.e. an empty checkout counter, or an empty conveyor belt. When analyzing an article the background spectrum is known and the processor may consider in different ways.

The linear camera of the contour sensor is preferably used in combination with the NIR camera to provide information of where the article is positioned on the belt. The NIR camera is movable along the slit between two conveyor belts but needs time to move into position for reading.

The VIS sensor is a spectrometer comprising a light device suitable for the mentioned wavelengths and a VIS camera capable of registering light of the wavelengths between 200 nm and 1100 nm. Similar to the NIR sensor the VIS sensor uses the change in wavelength when light is partly absorbed by or reflected by an article. The VIS sensor is particularly suitable for analyzing different shades of brown, which makes it suitable for analyzing bread which is normally hard to classify by means of any of the other sensors. The different shades of brown are detectable by the VIS sensor.

In this context "VIS sensor" may include the light source as well as the VIS camera, i.e. the complete VIS device for analyzing. However, the VIS sensor may also be a separate device, not connected to the light source, but including a light guiding probe and a spectrometer.

By analyzing a known article by means of a VIS sensor a unique reflection spectrum, VIS spectrum, is received, which may be coupled to the article. The reflection spectrum may either be used directly as a signature for the article, or the reflection spectrum may be processed for creating the signature. An article in a store may look different at different occasions, e.g. an article grow old (eventually fruit will rotten) and the article may be packed in one or several plastic bags or the article may be solitary or in a group, or being arranged in different orientations; natural variations of the article occurs also, etc. The environment for a checkout counter may also be different in different stores, e.g. different amount of light, color, etc. All these parameters provide that a VIS spectrum of a certain article in a certain environment at a certain occasion does not necessarily match with another VIS spectrum of the article in another environment at another occasion. To be able to use a VIS sensor according to the invention at a checkout counter a third signature, representing a background signature, and a fourth signature comprising background of article, has to match such that the processor is able to identify the article by a comparison. It is thus an advantage if the third signature is created in the same environment as the fourth signature. Since the fourth signature is created at the checkout counter during use, it is an advantage if the third signature is created under the same conditions. According to the invention, the classification system has thus a self-learning functionality in which the third signature is created by programming the memory unit with an article identity whereafter the article is transported trough the checkout counter during circumstances similar to use, i.e. circumstances for the checkout counter which refers to customer use. To consider the mentioned variations the article is transported several times through the checkout counter and in different variations, e.g. with one or several bags and/or solitary or in a group, etc. Each time the article is transported through the checkout counter and the VIS sensor is analyzing the article a third signature is created, which means that each article identity may be connected to a large amount of third signatures such that the processor will be able to identify the article when comparing it to the fourth signature and one or more of the third signatures. During learning the first VIS sensor may be arranged to perform the analyses, or a second VIS sensor will be connected. The learning does not need to be performed at the exact location where the checkout counter will be used but may rather be performed at another location.

The VIS sensor may comprise a fiber cable acting as a probe which distributes light from the article to the VIS camera.

The NIR sensor may comprise a fiber cable acting as a probe which distributes light from the article to the NIR camera.

Each of the VIS sensor and the NIR sensor may be connected to a fiber cable acting as probes which are arranged to converge into a common fiber cable which distributes light from the article to the VIS camera and the NIR camera.

The classification device may comprise a handheld barcode reader which is connected to the database. The handheld barcode reader may be used when articles are too big for the being conveyed on the conveying device.

The classification device may advantageously comprise a self-learning function which admits that the system becomes self-learning. "Self-learning" means that all sensors of the classification device become active for identification of an article when it passes the sensors for the first time. The sensors identify the properties/characteristics of the article and store the properties in the database. When the self-learning function is used the article is already registered in an article register with a predetermined identity, e.g. EAN code, and optionally price. The article register is either a part of the database or a separate database connected to the database of the article identity.

The classification device may be complemented by a barcode reader connected to the database and may preferably be used at the self-learning function. The first time the article is being transported through the classification device the fixed scanner reads the barcode which guarantees the identification of the article, which leads to that the properties being detected by the sensors are being stored in the database as the correct article identity.

The sensors may preferably be placed completely or partly in a tunnel shaped construction which shields a part of the conveyor belt and therefore improves the security by preventing unauthorized people from the possibility to affect the classification process.

DESCRIPTION OF THE DRAWINGS

Hereinafter, the invention will be described with reference to a number of drawings, wherein:

FIG. 1 schematically shows a top view of a checkout counter according to a first embodiment of the invention;

FIG. 2 schematically shows a side view of the checkout counter according to FIG. 1;

FIG. 5 schematically shows a top view of a checkout counter according to a third embodiment of the invention;

FIG. 6 schematically shows a side view of the checkout counter according to FIG. 5.

FIG. 7 schematically shows a top view of a checkout counter according to a fourth embodiment of the invention;

FIG. 8 schematically shows a side view of the checkout counter according to FIG. 7.

DESCRIPTION OF EMBODIMENTS

Figure 3:
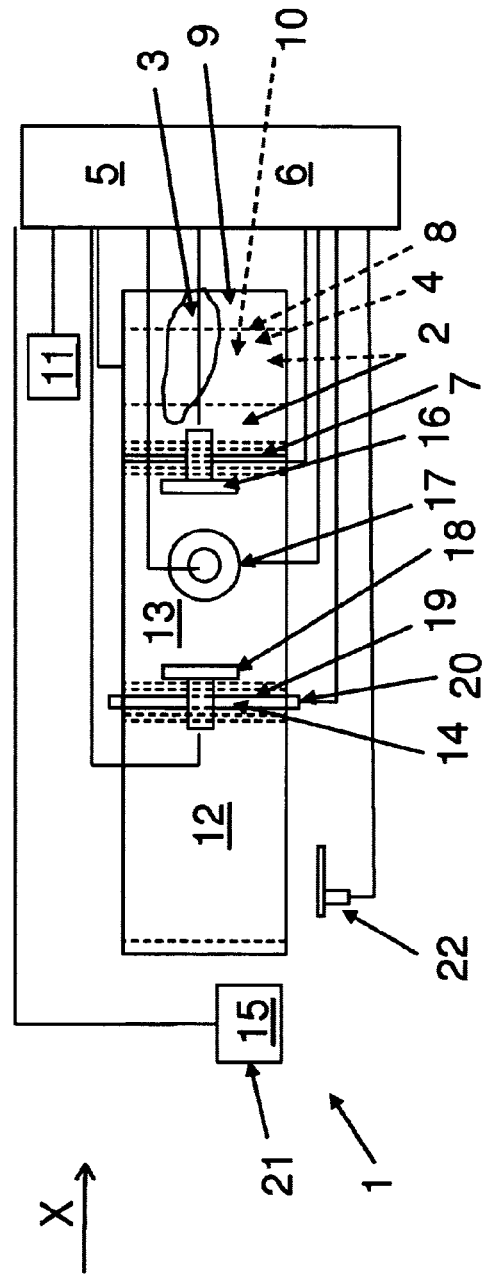
FIG. 3 schematically shows a top view of a checkout counter according to a second embodiment of the invention.

FIG. 1 schematically shows a view from above of a checkout counter according to a first embodiment of the invention.

FIG. 1 shows an automated checkout counter 1 comprising a classification device 2 for identifications of articles 3. The classification device 2 comprises a weight sensor 4 for weighing the article 3, a memory unit 5 comprising information of one or more articles, a processor 6 connected to the memory unit 5 and to the weight sensor 4, and a first spectroscopy sensor 7, from hereon denoted as a NIR or a VIS sensor 7 depending on the associated wavelength interval, connected to the processor 6. The memory unit 5 comprises one or more first signatures created by the first spectroscopy sensor 7 or another spectroscopy sensor (not shown), said first signature or which first signatures each being connected to a corresponding article identity. The first signatures may be created immediately at the checkout counter by using the first spectroscopy sensor 7 or a second spectroscopy sensor (not shown) or by loading the memory with signatures created by a spectroscopy sensor which is not connected to the checkout counter 1.

In FIG. 1 the weight sensor 4 is shown placed before the first NIR or VIS sensor 7, which means that the first NIR or VIS sensor is arranged to create a second signature after the article has been weighed, i.e. placed on the weight sensor and then weighed. The processor 6 is then arranged to compare the second signature with the first signature to identify the article 3 as one existing article identity in the memory unit 5. The weight of the article will be used by the processor together with the article identity to determine the price of the article.

As mentioned before a benefit of the invention is that the checkout counter automatically may identify all sorts of articles without any need for the customer to identify the article before the checkout counter, e.g. with a barcode. The NIR or VIS sensor is particularly valuable for identifying fruit and vegetables, and certain types of bulk articles, since these articles before have required the customer to identify the article and thereafter mark it due to the fact that sensors using cameras and image processing have not been able to determine the article identity.

Preferably, the weight sensor 4 comprises a conveyor scales 8 which automatically conveys the article and weighs it. The conveyor scale 8 comprises a first conveyor belt 9 and a scales unit 10 on which the conveyor belt rests. The customer puts the article on the first conveyor belt 9, wherein the scales unit 10 weighs the article and then the first conveyor belt conveys 9 away the article 3. An alternative is that the first conveyor belt 9 conveys the article 3 to an appropriate position, stops and weighs, and then further conveys the article 3. At the checkout counter 1, there are sensors arranged which give the processor information for control of the first conveyor belt 9 and the scales unit 10.

The first NIR or VIS sensor 7, or a NIR or VIS sensor (not shown) connected to the processor 6, may be arranged to read an article and create the first signature during a learning procedure when the article 3 already is identified for being able to be connected to the first signature.

FIG. 1 shows that the checkout counter 1 comprises an interactive display unit 11 connected to the processor 6 for displaying at least one article identity. The display unit 11 is arranged for use by one user to be able to approve the displayed information. If the first NIR or VIS sensor 7 identifies the article 3, an image or a text is shown in the display unit 11 and if the user finds the displayed information matching the article put in the checkout counter 1 the customer approves. Further information may be displayed, e.g. weight and price, wherein the user approves the displayed if it is correct.

In addition to the weight sensor 4, the first NIR or VIS sensor 7 and the display unit 11, FIG. 1 shows a second conveyor belt 12, and a third conveyor belt 13 for conveying the article 3. The direction of motion of the article on the conveyor belts is shown in FIGS. 1-8 by the reference sign x and an arrow which is shown in the direction of the motion. The purpose of several conveyor belts is that the article may be conveyed to a suitable final area where the article or articles may be picked up by the user after payment. Another purpose is that the checkout counter 1 may be designed in such a way that the weight sensor is placed after the first NIR or VIS sensor 7 (see FIGS. 3-8) or that the first NIR or VIS 7 sensor may be placed in a way that the first NIR or VIS sensor 7 may analyze the article while it at the same time is being weighed. The latter is not shown since it should be obvious, with the background of the embodiments shown in FIGS. 1-8, how the first NIR or VIS sensor 7 is being placed relative the scales unit. Further purpose for having several conveyor belts is if the checkout counter is provided with several sensors.

According to one embodiment of the invention the checkout counter 1 may, as a compliment to the first NIR or VIS sensor 7 and the weight sensor 4, be provided with one or several further sensors which, if used according to the invention, brings out the advantage of increasing the security when identifying the article, but with a minimum use of resources and time and energy. It should be mentioned here that an article 3 should preferably be identified in less than one second for an automated checkout counter to be considered as user friendly by the customers.

The present invention also aims at solving the problem with optimal use of resources for several sensors by using the sensors according to some predetermined combinations which provide high security when it comes to identifying the product as well as high processing speed. The combinations also provides the advantage that when a given combination is fulfilled, i.e. the sensor or the combined sensors provides a positive identification decision, the remaining sensors may be disconnected or be controlled towards identification of a further article, which provides an optimum of the processing resources.

Even though the invention is mainly based on the weight sensor 4 and a NIR or VIS sensor 7 according to the above, FIG. 1 shows that the checkout counter comprises several sensors which are connected in such a way that a number of predetermined combinations comprising partial set of existing sensors, are enough for a positive decision, i.e. identifying the article 3. It should be mentioned that the embodiment with further sensors provides a great amount of combinations and it is therefore not shown in separate figures because it would only lead to a great amount of figures without increasing the understanding of the invention.

The sensors may be switched on, i.e. activated, in sequences to be able to find beneficial combinations or a partial set of or all the sensors may be active until one of the combinations provides a positive decision, wherein one or more of the redundant sensors may be disconnected. A positive decision is here when all sensors in the combination have detected and indentified a predetermined property of an article, where the properties in combination together give the article an identity. The identity may be determined through control against a database comprising properties of an amount of articles. The database may be stored in the memory unit according to what has previously been described. Examples of properties are weight, size, color, shape, contour, marking with barcode and/or text and/or figure and/or pattern.

In order to provide a successful classification, an activated sensor determines a measured signature of an article 3. The measured signature is associated with the sensed signal, and may thus be a digital representation of a number of different article properties. The processor is for this purpose configured to compare the measured signature with the digital reference signatures stored in the memory unit 5, and to calculate a matching probability of a predetermined number of article identities.

The latter step is preferably performed by comparing the measured signature with all, or a subset of, the digital reference signatures of the memory unit and subsequently delivering the article identities having the highest matching probabilities to a further classification algorithm, such as a BBN classifier.

The activated sensor is preferably the spectroscopic sensor 7, 24, either NIR, VIS, or both NIR and VIS, implemented as a single array spectrometer operating in a well defined wavelength interval according to what has been previously described. Hence, the measured signature is a digital representation of the reflectance spectrum in the given wavelength interval.

The classification device may further use a further sensor being selected from the group consisting of: a spectroscopy sensor 24, a contour sensor 14, a barcode reader 15, a symbol reading sensor 16, a color texture sensor 17, a color histogram sensor 18, or a scale 4.

In case of using two or more different sensors thus providing two or more different measured signatures, the processor 6 is configured to determine specific article identities by comparing the matching probability from the different sensors 4, 7, 14, 15, 16, 17, 18, 24, and selecting the article identities having the highest matching probability. The article identities being identified by comparing the measured signature of the first sensor, as well as the article identities being identified by comparing the measured signature of the second or further sensor, are thus transmitted to the BBN network for further analysis. In this situation the article identities may not be exactly the same for the different sensors and the comparing analysis.

The classification method may further include a step of comparing the highest matching probability with an alarm threshold and, in case the highest matching probability is below the alarm threshold, awaiting manual input before proceeding.

In a preferred embodiment the method includes the step of comparing the highest matching probability with two alarm threshold wherein, in case the highest matching probability is below the lowest alarm threshold, the method awaits manual input from an attendant before proceeding, and in case the highest matching probability is above the lowest alarm threshold but below the upper alarm threshold, the method awaits manual input from a user before proceeding.

Further, if the scale 4 is used as a classifying sensor, the step of comparing the highest matching probability with an alarm threshold comprises the step of comparing the weight of the article with a weight interval associated with the article identity corresponding to the reference signature having the highest matching probability.

In a further embodiment, if the contour sensor 14 is used as a classifying sensor, the step of comparing the highest matching probability with an alarm threshold comprises the step of comparing the shape of the article with a shape interval associated with the article identity corresponding to the reference signature having the highest matching probability.

In a yet further embodiment, is the barcode reader 15 is used as a classifying sensor, the step of comparing the highest matching probability with an alarm threshold comprises the step of scanning a barcode of the article and comparing the information of the scanned barcode with barcode information associated with the article identity corresponding to the reference signature having the highest matching probability.

Figure 9:
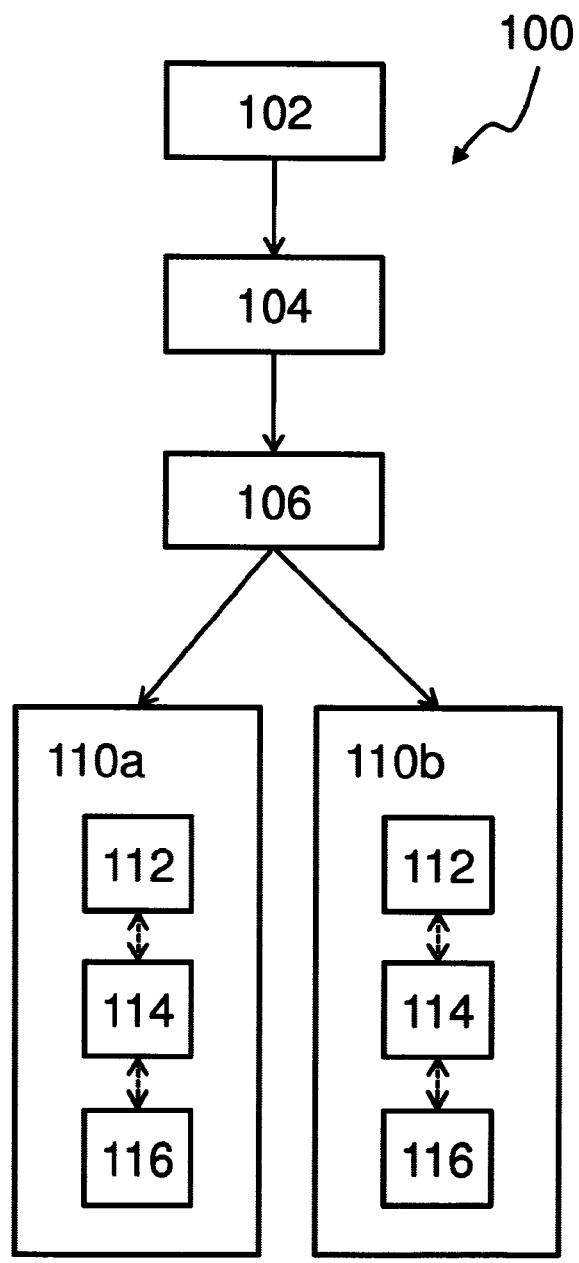
FIG. 9 is a schematic workflow of a method of a classification device according to an embodiment.

FIG. 9 shows a schematic flowchart of a classification algorithm 100 which may be implemented by a classification device. The algorithm comprises a number of steps for providing a successful classification of articles, e.g. in an automated checkout counter.

In step 102, a sensor determines a measured signature of an article. The measured signature is thereafter transmitted to a comparing unit, e.g. being incorporated in the processor 6, which comparing unit compares the measured signature with the digital reference signatures in a step 104. Following this, in a step 106 a matching probability of a predetermined number of article identities is calculated.

As an optional step 110a, the highest matching probability being calculated in step 106 is compared with an alarm threshold, and, in case the highest matching probability is below the alarm threshold, the method awaits manual input before proceeding.

As an alternative, the method 100 includes a step 110b in which the highest matching probability being calculated in step 106 is compared with two alarm thresholds wherein, in case the highest matching probability is below the lowest alarm threshold, the method awaits manual input from an attendant before proceeding, and in case the highest matching probability is above the lowest alarm threshold but below the upper alarm threshold, the method awaits manual input from a user before proceeding.

Steps 110a and 110b may further comprise sub steps 112, 114, and 116 respectively.

In step 112, the step of comparing the highest matching probability with an alarm threshold comprises the step of comparing the weight of the article with a weight interval associated with the article identity corresponding to the reference signature having the highest matching probability.

In step 114, the step of comparing the highest matching probability with an alarm threshold comprises the step of comparing the shape of the article with a shape interval associated with the article identity corresponding to the reference signature having the highest matching probability.

In step 116, the step of comparing the highest matching probability with an alarm threshold comprises the step of scanning a barcode of the article and comparing the information of the scanned barcode with barcode information associated with the article identity corresponding to the reference signature having the highest matching probability.

According to an embodiment, the classification device comprises: a weight sensor 4, a first NIR or VIS sensor 7, a contour sensor 15 and/or a barcode sensor 15 and/or a symbol reading sensor 16 which uses optical character recognition and (machine) text interpretation and/or a color texture sensor 17 and/or a color histogram sensor 18. The symbol reading sensor 16 is from hereon called OCR which is a general known abbreviation of the English expression "Optical Character Recognition". The sensors cooperate in such a way that if the sensors are activated in the following combinations the remaining sensors are allowed to deactivate or not be activated at all, depending on the article being identified:

weight sensor 4 and contour sensor 14 and OCR 16, or
contour sensor 14 and OCR 16, or
weight sensor 4 and OCR 16, or
weight sensor 4 and color histogram sensor 18 and contour sensor 14, or
weight sensor 4 and contour sensor 14 and OCR 16, or
weight sensor 4 and color histogram sensor 18 and contour sensor 14 and color texture sensor 17 and OCR 16 and barcode sensor 15, or
weight sensor 4 and contour sensor 14 and color texture sensor 17 and OCR 16 or
weight sensor 4 and barcode sensor 15, or
OCR 16.

The contour sensor 14 may comprise a camera for still or moving images, but may also comprise an object sensor. In FIG. 1, the contour sensor 14 is shown as a linear camera which is placed in the slit between the first conveyor belt and the second conveyor belt which reads a horizontal projected surface, in combination with an object sensor 20 which consists of a vertical light curtain for reading the vertical projection. The contour sensor 14 is connected to a unit for image processing where the contour, i.e. a two dimensional projection of a three dimensional object, is checked against the properties in the database.

In FIG. 1 an object sensor 20 comprising a light curtain device vertically standing at the slit between the first conveyor belt and the second conveyor belt 12 is shown. The light curtain device comprises a number of diodes with a transmitter on one side of the light curtain device and a receiver on the other side. Empirically it has been shown that the preferred amount of diodes is on the order of 32 diodes and that infrared diodes provide a good result. The invention is not limited to 32 diodes which are based on infra-red light, but any other number and frequency would work as long as the relative beams of the light curtain refract on different heights depending on the characteristics of the article and then provide information about the shape of the article. Since the article moves through the light curtain, a three dimensional image can be created by reading the light curtain at certain points of time.

FIG. 1 shows that the barcode sensor 15 comprises a camera for still or moving images, and that the symbol reading sensor 16 comprises a camera for still or moving images, and that the color texture sensor 17 comprises a camera for still or moving images, and a color histogram sensor 18 comprising a camera for still or moving images. The color histogram sensor 18 is preferably configured to detect three different color properties, namely i) HUE values, blob values, and topological values. The invention is not limited to the use of one or more cameras as long as the corresponding sensors may provide information to the processor which then may provide information about the article identity.

The classification device 2 further includes an initial sensor 21 which identifies the article 3 by 100% and is arranged to be used during learning of the system by first identifying the article 3 and subsequently conveying the article 3 through the classification device 2 where all of the sensors identify properties of the article 3, which properties will subsequently be stored in a database for properties of articles.

In FIG. 1 the initial sensor 21 is shown as the barcode reader 15 which is designed for manual use. The initial sensor 21 may however consist of another device which may provide the correct information to the memory unit. A user may for example manually enter the product name of the article or other information, e.g. price and/or price per weight, for each article. However, the barcode reader or another sensor admits that the system may be self-learned in a way that the articles are provided with a barcodes or other identification and then be fed into the system which automatically reads the identity and then lets the remaining sensors create its own signatures/recognition markers of the article.

FIG. 1 shows that the classification device comprises a handheld sensor 22 which by 100% identifies the article and which may be used when articles are too big for the remaining classification device. The handheld sensor may be a barcode reader intended for manual use.

FIG. 2 schematically shows a side view of the checkout counter according to FIG. 1.

FIG. 3 schematically shows a view from above of the checkout counter according to other embodiments of the invention. FIG. 3 shows the same arrangement as in FIG. 1 but with a difference in order of weight sensor 4 and the first NIR or VIS sensor 7. FIG. 3 shows that the weight sensor 4 is placed after the first NIR or VIS sensor 7. With reference to FIGS. 1 and 2, FIG. 3 shows that the different conveyor belts in the direction of movement of the conveyor belts are arranged after each other in the following order; the second conveyor belt 12, the third conveyor belt, and the first conveyor belt 9 with the weight unit. In FIG. 3 the display unit 11, as well as in FIGS. 1 and 2, is placed in connection to the weight sensor 4 so that a user will be able to approve an article in connection with the weighing. This is an advantage since the weight of the article is of importance for the price, which means that the customer would perceive a wrong price in connection to the weighing. The wrong price could be due to an incorrect identification of the article, and the user may at this location of the weight sensor 4 have the opportunity to change to the correct article and thereby get the correct price through a new or continued weighing connected to the correct article identity. In FIG. 3 the contour sensor 14 is placed between the second 12 and the third conveyor belt 13 and the first NIR or VIS sensor 7 between the third conveyor belt 13 and the first conveyor belt 9.

Figure 4:
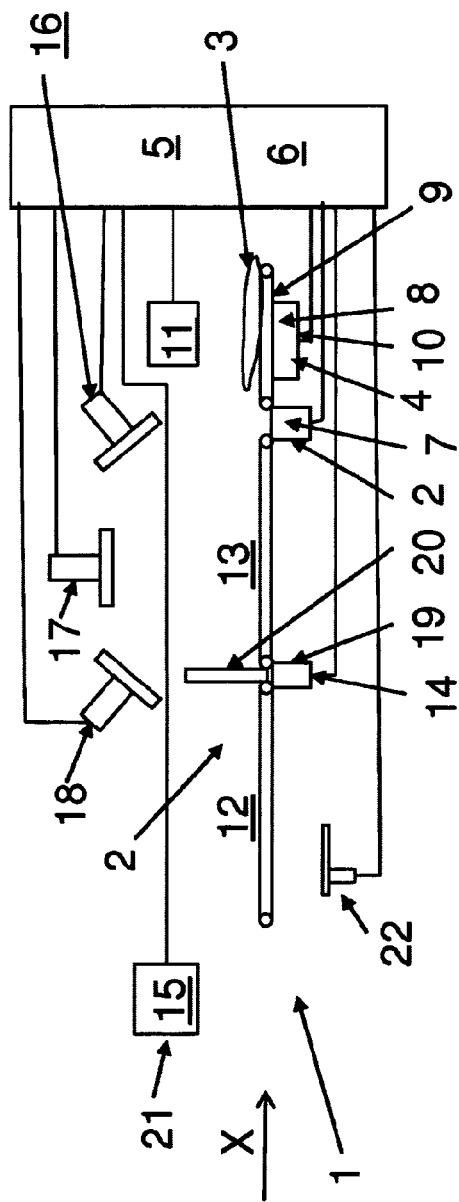
FIG. 4 schematically shows a side view of the checkout counter according to FIG. 3.

FIG. 4 schematically shows a side view of the checkout counter according to FIG. 3.

FIG. 5 schematically shows a view from above of a checkout counter according to a third embodiment of the invention. FIG. 5 shows the same arrangement as in FIGS. 3 and 4, but with the addition of a camera 23 placed in connection to the scales unit 10 to be able the capture an image of the article. The image should be displayed to the customer via the display unit 11 so that the customer may be able to actively decide if the first NIR or VIS sensor has correctly identified the article. The image may also be displayed to a controller who is sitting at a distance and who is able to decide if the first NIR or VIS sensor has read it correctly. In the case where several sensors are connected to the checkout counter 1, the same reasoning applies regarding the image being used by the customer or the controller to determine if the article has been correctly identified. To speed up the identification process and also make it more robust, the classification device may comprise a function for uncertainty of the article identity, where many options are displayed to the customer via the display unit. The customer may then choose the correct option. In this context the above mentioned image may be used together with the displayed information about the different options to facilitate the identification, since the stored images of the article may be easier to compare with the image of the article then with the article placed in the checkout counter.

FIG. 6 schematically shows a side view of the checkout counter according to FIG. 5.

FIG. 7 schematically shows a view from above of a checkout counter according to a fourth embodiment of the invention. FIG. 7 shows the same devices as FIGS. 5 and 6, but with the addition of a further spectroscopy sensor 24 being arranged between the first conveyor belt 9 and the second conveyor belt 13 to identify the product by means of spectroscopy. Preferably, the further spectroscopy sensor 24 is a complement to the first spectroscopy sensor 7, such that if the first spectroscopy sensor 7 is a NIR sensor, i.e. detecting light having a wavelength between 780 nm and 2500 nm, the further spectroscopy sensor 24 is a VIS sensor, i.e. detecting light having a wavelength between 200 nm and 1100 nm. Consequently, if the first spectroscopy sensor 7 is a VIS sensor the further spectroscopy sensor 24 is a NIR sensor. The further spectroscopy sensor 24, in this case a VIS sensor, as well as the first spectroscopy sensor 7, in this case a NIR sensor, may comprise a fiber cable which distributes light from the article to the respective sensor. The fiber cable is a light guide acting as a probe. The VIS sensor and the NIR sensor may both be connected to a separate fiber cable which are arranged to converge into a common fiber cable which distributes light from the article to the VIS sensor and to the NIR sensor, respectively.

The probe, being provided to transmit light from the article 3 to the spectroscopy sensor 7, 24 is arranged to be moveable laterally relative a conveyor belt (9, 12, 13) of the device. The probe is connected to the spectroscopy sensor 7, 24, preferably being a single array spectrometer configured to operate in a wavelength interval according to what has been described above. That is, the spectroscopy sensor may either be a VIS sensor, a NIR sensor, or a combined NIR and VIS sensor.

The classification device may further comprise a detector configured to detect the lateral position of the article 3 on the conveyor belt 9, 12, 13, and a controller connected to said detector and being configured to move said at least one sensor probe 7 to a position corresponding to said detected lateral position of the article 3. This may be done by detecting the article 3 and calculating the lateral position corresponding to the mean value of the volume of the article. The detector may thus be camera, or any other optical sensor being connected to an image processing device for calculating the mean value of the volume.

The detector may further be configured to detect several positions of the article 3 as the article 3 is moving along the conveyor belt 9, 12, 13 such that said at least one sensor probe 7 is sequentially moved to the positions corresponding to said detected lateral positions of the article 3. Hence, if an article 3 is not aligned with the lateral or longitudinal direction of the conveyor belt 9, 12, 13, the probe will be moved during the article movement for providing measured signatures at different positions of the article.

The classification device further comprises a light source for illuminating said article 3, wherein the emitted light has a wavelength distribution covering at least the operating wavelengths of the spectroscopy sensors 7, 24. Preferably, the light source is also moveable laterally relative said conveyor belt 9, 12, 13 such that the article 3 is sufficiently illuminated when the spectroscopy sensors are activated.

The detector may further be triggered by an object sensor 20 configured to detect the presence of an article 3 on said conveyor belt 9, 12, 13. Hence, the light source and the probes of the spectroscopy sensor(s) 7, 24 may be positioned in an idle position until the object sensor 20 triggers the detector, whereby the light source and the probes are moved to the position corresponding to the mean value of the article's volume.

The probes as well as the light source may be arranged on a linear stage arranged in a transverse direction of said conveyor belt 9, 12, 13 for providing the moving functionality.

As the probes are moveable, the spectroscopy sensors, i.e the spectrometers, may be fixedly arranged at a remote position for reducing vibrations and other noise which may affect the spectroscopic analysis negatively. However, the spectrometers may also be mounted to the moving stage.

The VIS sensor 24 may be arranged at a checkout counter according to any one of FIGS. 1-6 and may be arranged at the first conveyor belt 9, the second conveyor belt 12, or the third conveyor belt 13.

When the VIS sensor 24 is turned on it is configured to operate in the intervals from 200 nm to 400 nm and from 660 nm to 1100 nm if it is used in combination with the color texture sensor 17 and/or the color histogram sensor 18, but is configured to operate in the interval from 200 nm to 1100 nm when the color texture sensor 17 and the color histogram sensor are disconnected. The processor 6 is arranged to control the intervals of the VIS sensor depending on whether the color texture sensor and/or the color histogram sensor are turned on or off. The VIS sensor 24 may be used in combination with any of the mentioned combinations with reference to FIGS. 1-6, or only in combination with the weight sensor 4 and the first NIR sensor 7.

The VIS sensor 24 is connected to the processor 6 and to the memory unit 5. The memory unit comprises one or several third signatures created by the VIS sensor 24 or by another VIS sensor (not shown). The third signature or the first signatures are each connected to a corresponding article identity. The third signatures may be created directly at the checkout counter by using the VIS sensor 24 or another VIS sensor (not shown), or by loading the memory with signatures being created by a VIS sensor not being connected to the checkout counter 1.

FIG. 7 shows that the weight sensor 4 is arranged after the VIS sensor 24, which means that the VIS sensor 24 is arranged to create a fourth signature by means of analysis before the article has been weighed, i.e. being arranged on the weight sensor 4 and subsequently being weighed. The processor 6 is thereafter arranged to compare the fourth signature with the third signature in order to identify the article 3 as an existing article identity in the memory unit 5. The weight of the article 3 is used by the processor, together with the article identity, for determining the price of the article 3.

FIG. 8 schematically shows a side view of the checkout counter in FIG. 7.

It shall be noted that the examples shown in FIGS. 1-8 are not limiting for the invention, but only example of placements of sensors and conveyor belts. The checkout counter according to the invention may comprise one or several conveyor belts. In case of several conveyor belts, they may be angled towards each other and/or arranged for splitting a flow of articles into partial flows etc. Adding more sensors to the checkout counter than the first spectroscopy sensor and the weight sensor may be seen as further possibilities for improved identification and is thus a complement to the described embodiment with the first spectroscopy sensor and the weight sensor. The additional sensors may be placed in a vast amount of ways besides what is shown in FIGS. 1 to 8 for providing acceptable results within the scope of the invention.

The invention claimed is:

1. A classification device for identification of articles in an automated checkout counter, comprising:
   a memory unit capable of storing digital reference signatures, each of which digital reference signatures corresponds to an article identity,
   a processor connected to the memory unit, and
   at least two different sensors configured to determine a measured signature of an article, wherein at least one said sensor is a spectroscopy sensor in the form of a spectrometer configured to operate in a wave length interval of 850-2500 nm, wherein the measured signature determined from the at least one sensor is a digital representation of a reflectance spectrum in the wave length interval;
   wherein said processor is configured to compare said measured signature with the digital reference signatures, and to calculate a matching probability of a predetermined number of article identities, wherein the processor is configured to determine the article identities by comparing the matching probability from the different sensors and selecting the article identities having the highest matching probability from at least one of the different sensors regardless of whether any of the article identities associated with the different sensors are the same.

2. The classification device according to claim 1, wherein said spectrometer is a single array spectrometer.

3. The classification device according to claim 1, further comprising a further sensor being selected from the group consisting of: a spectroscopy sensor, a contour sensor, a barcode reader, a symbol reading sensor, a color texture sensor, a color histogram sensor, or a scale.

4. The classification device according to claim 1, comprising at least two different sensors, wherein said processor is configured to determine specific article identities by comparing the matching probability from the different sensors, and selecting the article identities having the highest matching probability.

5. The classification device according to claim 1, wherein the classification device is incorporated in to an automated checkout counter.

6. A method for classifying articles in an automated checkout counter, comprising the steps of:
provinding a classification device comprising a memory unit capable of storing digital reference signatures, each of which digital reference signatures corresponds to an article identity, a processor connected to the memory unit, and at least two different sensors configured to determine a measured signature of an article, wherein said sensor is a spectroscopy sensor in the form of a spectrometer configured to operate in a wave length interval of 850-2500 nm, wherein the measured signature determined from the at least one sensor is a digital representation of a reflectance spectrum in the wave length interval,
comparing said measured signature with the digital reference signatures
calculating a matching probability of a predetermined number of article identities; and
determining the article identities by comparing the matching probability from the different sensors and selecting the article identities having the highest matching probability from at least one of the different sensors regardless of whether any of the article identities associated with the different sensors are the same.

7. The method according to claim 6, further comprising:
comparing the highest matching probability with an alarm threshold and, in case the highest matching probability is below the alarm threshold, awaiting manual input before proceeding.

8. The method according to claim 7, further comprising:
comparing the highest matching probability with a two alarm threshold,
in case the highest matching probability is below the lowest alarm threshold, awaiting manual input from an attendant before proceeding, and
in case the highest matching probability is above the lowest alarm threshold but below the upper alarm threshold, awaiting manual input from a user before proceeding.

9. The method according to claim 7, wherein the step of comparing the highest matching probability with an alarm threshold comprises the step of comparing the weight of the article with a weight interval associated with the article identity corresponding to the reference signature having the highest matching probability.

10. The method according to claim 7, wherein the step of comparing the highest matching probability with an alarm threshold comprises the step of comparing the shape of the article with a shape interval associated with the article identity corresponding to the reference signature having the highest matching probability.

11. The method according to claim 7, wherein the step of comparing the highest matching probability with an alarm threshold comprises the step of scanning a barcode of the article and comparing the information of the scanned barcode with barcode information associated with the article identity corresponding to the reference signature having the highest matching probability.

* * * * *